United States Patent [19]

Cavallotti et al.

[11] Patent Number: 5,310,934
[45] Date of Patent: May 10, 1994

[54] PROCESS FOR PURIFYING PHTHALIMIDOPEROXYCAPROIC ACID (PAP) IN ORDER TO REMOVE CHLORINATED SOLVENT IMPURITIES FROM IT

[75] Inventors: Claudio Cavallotti; Claudio Troglia, both of Milan; Roberto Garaffa, Napoli, all of Italy

[73] Assignee: Ausimont S.p.A., Milan, Italy

[21] Appl. No.: 19,789

[22] Filed: Feb. 19, 1993

[30] Foreign Application Priority Data

Feb. 21, 1992 [IT] Italy ............... MI 92 A 000381

[51] Int. Cl.$^5$ ................................. C07D 209/48
[52] U.S. Cl. ................................. 548/479
[58] Field of Search ......................... 548/479

[56] References Cited

U.S. PATENT DOCUMENTS 4,172,086 10/1979 Berkowitz ............... 260/406

FOREIGN PATENT DOCUMENTS

0325288A1  1/1989  European Pat. Off. ....... 548/479
0490409A1 12/1991  European Pat. Off. ....... 260/502
3823172A1 11/1990  Fed. Rep. of Germany ... 548/479
4003309A1  8/1991  Fed. Rep. of Germany ... 548/479
2385697    3/1978  France ..................... 260/406
WO90/07501 7/1990  PCT Int'l Appl. .......... 548/479
WO90/14336 11/1990 PCT Int'l Appl. .......... 548/479

OTHER PUBLICATIONS

CA116:257898d Stable . . . granules. Gethoeffer et al., 134, 1992.
CA117:92681h Storage-stable bleach compositions. Aoyanagi et al., 135, 1992.
CA117:114058q Liquid . . . per acid. Buskirk et al., 132, 1992.
CA117:150885r Process . . . acid. Cavallotti et al., 1992.

Primary Examiner—Mary C. Lee
Assistant Examiner—Joseph K. McKane
Attorney, Agent, or Firm—Bryan Cave

[57] ABSTRACT

Process for purifying phthalimido-peroxycaproic acid (PAP) from chlorinated solvents, by dissolving it in a polar and volatile solvent selected from alcohols, ketones and aliphatic esters, and a following crystallization thereof and solvent stripping.

Preferred solvents are aliphatic esters, in particular ethyl acetate.

5 Claims, No Drawings

PROCESS FOR PURIFYING PHTHALIMIDOPEROXYCAPROIC ACID (PAP) IN ORDER TO REMOVE CHLORINATED SOLVENT IMPURITIES FROM IT

The present invention relates to a process for purifying phthalimido-peroxycaproic acid (PAP) from the impurity constituted by the chlorinated solvents used in the synthesis and entrapped inside PAP crystal lattice.

More in particular, the present invention relates to a process for purifying PAP in which the chlorinated solvents, which constitute the impurity, are removed by means of a solvent showing particular characteristics.

The process for preparing PAP is known from U.S. Pat. No. 5,208,480.

According to this process, phthalimido-caproic acid (PAC) is converted into peroxy acid, by means of $H_2O_2$, in the presence of a strong acid, in a double phase system, in the presence of an organic solvent constituted by a halogenated aliphatic hydrocarbon selected from dichloromethane and trichloromethane. The resulting PAP is recovered from the organic phase by low-temperature crystallization, or solvent removal under vacuum (stripping).

By means of analyses of the end product (PAP) (gas-chromatography, X-ray fluorescence), the presence of the chlorinated solvents used for the synthesis, was determined. PAP crystals contain such entrapped solvents in an amount comprised within the range of from 500 to 2,500 ppm.

It is known that the halogenated aliphatic compounds are toxic and potentially carcinogenic; they may consequently create pollution problems. Therefore, the content of chlorinated solvents entrapped inside PAP should advisably be reduced down to an extremely low level in all products designed for consumer's usage. Such a reduction or removal is recommended in the case of industrial use of PAP as a bleaching agent in medium-low temperature detergent compositions.

The purpose of the present invention is hence of providing a process which can be performed at an industrial level, in order to eliminate the impurities constituted by the chlorinated solvents entrapped inside the crystal lattice of PAP, obtained according to the process as disclosed in U.S. Pat. No. 5,208,480.

The present Applicant found now that the use of a solvent, used after the synthesis of PAP and showing particular characteristics, makes it possible the chlorinated solvents present inside PAP's crystal lattice, also at an industrial level.

Therefore, the subject-matter of the present invention is a process for purifying phthalimido-peroxycaproic acid (PAP) from chlorinated solvents, by dissolving said PAP and subsequent crystallization and evaporation of the solvents (stripping), characterized in that said PAP is dissolved in a polar and volatile solvent, selected from the group consisting of alcohols, ketones and aliphatic esters.

More in particular, an object of the present invention is a process for purifying PAP from chlorinated solvents by means of a dissolution thereof and subsequent crystallization or evaporation of solvents (stripping), characterized in that said PAP is dissolved in a solvent belonging to the class of aliphatic esters.

The choice of the solvent used for PAP purification according to the present process is critical.

The solvents suitable for the purposes of the present invention must meet the following requisites:

they should be good solvents for PAP and for the chlorinated solvent used in the synthesis and entrapped inside the crystals of the obtained PAP;

they should display good volatility, in order to facilitate the removal of the solvent from the peracid, which volatility however should be not excessively high, in order to jeopardize a possible industrial use thereof;

they should be not toxic, in order to prevent that a further toxic solvent is entrapped inside PAP crystal;

they should be completely inert towards the peracid, and display an extremely good oxidation resistance, because the residual traces of solvent used (from 100 to 800 ppm) remaining inside the end product, or of its oxidation products, could, besides creating safety problems, remain inside the peracid crystals, reducing the stability thereof (for example, esters, when into contact with oxygen, form peroxides).

The used solvents, which meet the above mentioned requisites, required by the process according to the present invention, are polar and volatile solvents. In particular, these solvents are aliphatic esters, such as methylacetate and ethylacetate. Preferred solvent is ethylacetate.

The ratio, by weight, of the peracid and the solvent used in order to dissolve it according to the process of the present invention is determined by the solubility of the peracid in the solvent, and preferably is comprised within the range of from 1:2 to 1:8. When aliphatic esters are used as solvents, this ratio is preferably comprised within the range of from 1:3 to 1:6.

The temperature at which the subject process is carried out, is lower than 40° C., in order to prevent peracid decomposition.

In the process according to the present invention, the crystallization or the solvents evaporation (stripping) may take place both in the presence and in the absence of demineralized water. The peracid is separated in crystal form.

The PAP obtained according to the process of the present invention contains less than 3 ppm of chlorinated solvents. PAP deprived of the chlorinated solvents is stable, in particular when as the solvent in the process according to the present invention, aliphatic esters are used.

According to a preferred embodiment, PAP containing the impurity constituted by a chlorinated solvent is dissolved in a solvent belonging to the class of aliphatic esters, and the purification is carried out by using methodologies known in the art, at a temperature lower than +40° C.

In order to better understand the present invention and to practice it, some illustrative, non-limitative examples are reported in the following.

EXAMPLES 1-4

50 g of PAP was dissolved in each of the solvents reported in following Table 1, at a temperature lower than +40° C.

So dissolved PAP was treated by means of well-known methodologies [(a) and (b)] in order to recover PAP practically free from chlorinated solvents.

(a) According to the crystallization methodology, dissolved PAP was recrystallized at the temperature of 0° C. The resulting crystals were filtered off from the suspension, and were subsequently dried in a desicator (CaCl$_2$) for 24 hours at the temperature of +25° C., under vacuum.

(b) According to the stripping methodology, dissolved PAP was fed, either continuously or batchwise, to a reactor, or to the kettle of a rotary evaporator, at a temperature lower than +40° C. PAP solution was kept at this temperature under such a residual pressure as to cause the evaporation of the solvent. The peracid was subsequently filtered off, was dried inside a desiccator (CaCl$_2$) under vacuum for 24/48 hours at room temperature.

The operations carried out with the above disclosed [(a) and (b)] methodologies were carried out both in the presence (Examples 2 and 4) and in the absence of demineralized water (Examples 1 and 3).

The process conditions and the results obtained are reported in Table 1.

The operating conditions and the results obtained are reported in Table 2.

TABLE 2

| Example No. | Solution fed to purification | | | | Operating conditions | | | Obtained PAP, as dry matter | | | |
|---|---|---|---|---|---|---|---|---|---|---|---|
| | Used solvent | | PAP to be purified | | Dissolution temperature °C. | Stripping temperature °C. | Residual pressure mmHg | A-mount, g | Purity % | Chloromethanes, ppm | Residual solvent ppm |
| | Type | Amount, g | Purity % | Chloromethanes, ppm | | | | | | | |
| 5 | Ethanol | 150 | 98.8 | 1,900 | 35° C. | — | — | 38 | 99.5 | <1 | 680 |
| 5 | Ethanol | 200 | 98.5 | 1,730 | 35° C. | 37° C. | 20 | 49 | 98.4 | <1 | 590 |
| 6 | Acetone | 188 | 98.5 | 950 | 30° C. | — | — | 30 | 99.2 | 2 | 630 |
| 6 | Acetone | 188 | 98.5 | 950 | 30° C. | 37° C. | 20 | 49.5 | 98.5 | <1 | 370 |

Stability of Purified PAP

The thermal stability of purified PAP was determined by DSC (differential scanning calorimetry) according to ASTM method No. E-537-84 using a PERKIN-ELMER DSC-2C instrument, as well as the loss of peroxide content (%) of said purified peroxide acid.

In order to determine this loss, the tests (A) and (B) were carried out.

According to test (A), 10 g of purified PAP were stored inside a tightly ceiled container, for 30 days at +25° C.

According to test (B), 0.3 g of purified PAP were stored as a suspension in an inert hydrocarbon (diisopropylbenzene) for 1 hour at +70° C. The results obtained by examining PAP purified according to Examples 1–6 are reported in following Table 3.

TABLE 1

| Example No. | Solution fed to purification | | | | Operating conditions | | | Obtained PAP, as dry matter | | | |
|---|---|---|---|---|---|---|---|---|---|---|---|
| | Used solvent | | PAP to be purified | | Dissolution temperature °C. | Stripping temperature °C. | Residual pressure mmHg | A-mount, g | Purity % | Chloromethanes, ppm | Residual solvent ppm |
| | Type | Amount, g | Purity % | Chloromethanes, ppm | | | | | | | |
| 1 | Methyl acetate | 280 | 99.1 | 1,200 | 30° C. | — | — | 37.5 | 99.7 | <1 | 690 |
| 2 | Methyl acetate (H$_2$O) | 260 | 99.1 | 1,200 | 30° C. | 35° C. | 100 | 49 | 99.2 | 3 | 750 |
| 3 | Ethyl acetate | 280 | 98.7 | 1,350 | 35° C. | — | — | 35.5 | 99.3 | <1 | 800 |
| 3 | Ethyl acetate | 280 | 98.9 | 2,300 | 35° C. | 37° C. | 20 | 49 | 98.9 | <1 | 400 |
| 4 | Ethyl acetate + 4% (H$_2$O) | 263 | 98.5 | 1,730 | 25° C. | — | — | 35.5 | 99.3 | 2 | 650 |
| 4 | Ethyl acetate (H$_2$O) | 263 | 98.5 | 1,730 | 25° C. | 35° C. | 60 | 48.5 | 98.6 | <1 | 480 |

TABLE 3

| | Purified PAP | | | Stability | | | |
|---|---|---|---|---|---|---|---|
| | | | | D.S.C. | | Loss of peroxide content (%) | |
| Example No. | Residual chloromethanes, ppm | Residual solvent | | Incipient melting point, °C. | Incipient decomposition, °C. | | |
| | | Type | ppm | | | Test (A) | Test (B) |
| 1 | <1 | methyl acetate | 690 | — | 89.5 | 3.5 | 7.4 |
| 2 | 3 | methyl acetate (H$_2$O) | 750 | 65 | 90.5 | 3.2 | 7.3 |
| 3 | <1 | ethyl acetate | 800 | 68.3 | 93.8 | 0 | 4.7 |
| 3 | <1 | ethyl acetate | 400 | 73.1 | 94.8 | 0 | 4.5 |
| 4 | 2 | ethyl acetate + H$_2$O 4% | 650 | 71.8 | 94.2 | 0 | 4.6 |
| 4 | <1 | ethyl acetate (H$_2$O) | 480 | 68.3 | 94 | 0 | 4.6 |
| 5 | <1 | ethanol | 680 | 64.9 | 85.4 | 47 | 12.9 |
| 5 | <1 | ethanol | 590 | 64.5 | 86.1 | 44 | 12.9 |
| 6 | 2 | acetone | 630 | — | 88.3 | 12 | 9.3 |
| 6 | <1 | acetone | 370 | 65.1 | 88.7 | 10 | 9.2 |

EXAMPLES 5–6

The operating modalities of Examples 1–4 were repeated, however using, as the solvent in PAP purification, an alcohol (ethanol) and a ketone (acetone).

Stripping and crystallization were carried out in the absence of H$_2$O.

The data reported in Table 1, 2 and 3 demonstrate that the process according to the present invention removes the impurity constituted by dichloromethane from PAP. The PAP obtained by using the aliphatic esters as the solvent of the process according to the present invention, is very stable.

EXAMPLE 7

Comparison Example

The hexane used for comparison purposes would be capable of dissolving the chlorohydrocarbon impurity entrapped inside PAP crystals, but does not dissolve said PAP and therefore does not meet the requisites required by the solvent to be used in the process according to the invention.

The operating modalities of Examples 1–4 were repeated using n-hexane as the solvent, and separating PAP by stripping at the temperature of $+37°$ C. The residual pressure was of 20 mmH g.

The operating conditions and the results obtained are reported in Table 4.

The data shown in Table 4 demonstrate that dichloromethane was not removed from PAP, therefore the purification did not occur.

TABLE 4

| | Solution sent to purification | | | | Obtained PAP in dry state | | | |
| --- | --- | --- | --- | --- | --- | --- | --- | --- |
| | Used solvent | | PAP to be purified | | | | | |
| Example No. | Type | Amount, g | Purity, % | Chloromethane content, ppm | Amount, g | Purity, % | Chloromethane content, ppm | Residual solvent, ppm |
| 7 | n-Hexane | 400 | 98.7 | 1,350 | 50 | 98.6 | 1,290 | 800 |

We claim:

1. A process for purifying phthalimido-peroxycaproic acid (PAP) from chlorinated solvents, said process comprising:
   (a) dissolving said PAP in a non-chlorinated polar and volatile solvent selected from the group consisting of alcohols, ketones and aliphatic esters; and
   (b) recovering said PAP by recrystallization from said non-chlorinated polar and volatile solvent or by evaporating said non-chlorinated polar and volatile solvent; said process being carried out at a temperature lower than $+40°$ C.

2. The process of claim 1, wherein said non-chlorinated polar and volatile solvent is an aliphatic ester.

3. The process of claim 1, wherein said non-chlorinated polar and volatile solvent is ethyl acetate.

4. The process of claim 1, wherein the ratio of the PAP to the non-chlorinated polar and volatile solvent is within the range of from 1:2 to 1:8 by weight.

5. The process of claim 4, wherein the ratio of the PAP to the non-chlorinated polar and volatile solvent is within the range of from 1:3 to 1:6 by weight.

* * * * *